(12) United States Patent
Lee et al.

(10) Patent No.: US 7,063,777 B2
(45) Date of Patent: Jun. 20, 2006

(54) DIELECTROPHORETIC PARTICLE PROFILING SYSTEM AND METHOD

(75) Inventors: Richard Stanley Lee, Mountain View, CA (US); Ronald Pethig, Mountain View, CA (US); Mark Stuart Talary, San Jose, CA (US)

(73) Assignee: Aura BioSystems Inc., Taipei (TW)

( * ) Notice: Subject to any disclaimer, the term of this patent is extended or adjusted under 35 U.S.C. 154(b) by 448 days.

(21) Appl. No.: 10/319,860

(22) Filed: Dec. 12, 2002

(65) Prior Publication Data

US 2004/0112748 A1    Jun. 17, 2004

(51) Int. Cl.
*G01N 27/447*    (2006.01)
*G01N 27/453*    (2006.01)

(52) U.S. Cl. .................... 204/547; 204/643
(58) Field of Classification Search .............. 204/547, 204/643
See application file for complete search history.

(56) References Cited

U.S. PATENT DOCUMENTS

| | | | |
|---|---|---|---|
| 4,390,403 A | 6/1983 | Batchelder | 204/180 R |
| 4,956,065 A | 9/1990 | Kaler et al. | 204/183.1 |
| 5,059,909 A * | 10/1991 | O'Brien | 324/457 |
| 5,454,472 A | 10/1995 | Benecke et al. | 209/127.1 |
| 5,569,367 A | 10/1996 | Betts et al. | 204/547 |
| 5,626,734 A | 5/1997 | Docoslis et al. | 204/547 |
| 5,795,457 A | 8/1998 | Pethig et al. | 204/547 |
| 5,814,200 A | 9/1998 | Pethig et al. | 204/547 |
| 5,993,631 A * | 11/1999 | Parton et al. | 204/547 |
| 6,264,815 B1 | 7/2001 | Pethig et al. | 204/547 |
| 6,467,630 B1 | 10/2002 | Zborowski et al. | |
| 6,858,439 B1 * | 2/2005 | Xu et al. | 436/518 |
| 2002/0125138 A1 | 9/2002 | Medoro | 204/547 |

FOREIGN PATENT DOCUMENTS

| | | |
|---|---|---|
| GB | 2 238 619 A | 6/1991 |
| WO | WO 95/17258 | 6/1995 |
| WO | WO 01/05512 A1 | 1/2001 |
| WO | WO 01/83113 A1 | 11/2001 |

OTHER PUBLICATIONS

Cruz et al. (Dielectrophoretic motion of oblate spheroidal particles. Measurements of motion of red blood cells using the Stokes method, J. Phys. D: Appl. Phys. 31 (1998) 1745-1751).*

Wang et al. (Theoretical and experimental investigations of the interdependence of the dielectric, dielectrophoretic and electrorotational behaviour of colloidal particles, J. Phys. D: Appl. Phys. 26 312-22).*

(Continued)

*Primary Examiner*—Alex Noguerola
(74) *Attorney, Agent, or Firm*—Fish & Richardson P.C.

(57) ABSTRACT

An apparatus and methods for determining the dielectrophoretic response of particles under various chemical and physical conditions are disclosed.

53 Claims, 8 Drawing Sheets

OTHER PUBLICATIONS

Cruz et al. Dielectrophoretic Force Measurements in yeast cells by the Stokes method. IEEE Inducstry Applications Society Annual Meeting, New Orleans, LA 10/5-Jul. 1997, pp. 2012-2018.

Gascoyne et al., "Particle separation by dielectrophoresis," Electrophoresis, 23:1973-1983, 2002.

Huang et al., "Membrane changes associated with . . . ," Biochimica et Biophysica Acta, 1282:76-84, 1996.

Huang et al., "Dielectrohoretic Cell Separation . . . ," Anal. Chem. 74:3362-3371, 2002.

Pethig , Ronald, "dielectrophoresis: Using Inhomogeneous . . . ," Critical Reviews in Biotechnology, 16(4):331-348, 1996.

Wang et al., "Membrane dielectric changes indicate . . . ," Biochimica et Biophysica Acta, 1564:412-420, 2002.

* cited by examiner

DIELECTROPHORETIC PARTICLE PROFILING SYSTEM AND METHOD

TECHNICAL FIELD

This invention relates to dielectrophoresis.

BACKGROUND

Dielectrophoresis ("DEP") refers to the force experienced by particles suspended in a fluid medium in applied electric field gradients. Due to the electric field gradient, differences in the dielectric polarization between the particles and the fluid medium cause the particles to experience a dielectrophoretic force. This effect can be quantified in terms of the electromagnetic momentum balance via the Maxwell stress tensor, or in terms of the magnitude and distribution of the charges induced on and within the particle by the applied field. Particles, such as blood cells, experiencing strong DEP motion will typically experience a DEP force of about $10^{-11}$ N, which is about 40 times greater than the gravitational settling force and about $2 \times 10^5$ times larger than the maximum Brownian diffusion force.

A particle's structural and physico-chemical properties can contribute towards its DEP response. This response can also depend on the frequency of the applied electric field. Due to these dependencies, variations in applied field frequencies and external environment can simultaneously probe different particle substructures and processes. For example, some fundamental electrical properties of cells, such as membrane capacitance, membrane resistance and cytoplasmic conductance affect their DEP response. These properties also reflect a cell's ability to maintain ion balances and are a measure of metabolic work and biological organization. Thus, DEP can provide a non-invasive method for determining the electrical properties of cell populations, down to the single cell level.

Accordingly, DEP has potential uses in a number of fields. For example, DEP can be used as a drug discovery tool, e.g., monitoring the dielectrophoretic response of a cell population to candidate chemical compounds. Other potential applications include separating particle populations using their differing dielectrophoretic response.

SUMMARY

In order to be effective in the above-mentioned and other applications, a DEP system should provide accurate and efficient characterization of particle populations, with reasonable throughput and versatility. Accordingly, in certain aspects, the invention features an apparatus and method for monitoring the dielectrophoretic response of one or more particles by capturing video sequences of the particles under the influence of varying DEP forces, and using image analysis to determine the response of each particle to the field. In preferred embodiments, the image analysis includes determining particle velocities as a function of electric field frequency for a known field profile, and determining the dielectrophoretic force on each particle from the particle size and velocity.

Various aspects of the invention will now be summarized.

In general, in a first aspect, the invention features a method that includes (i) sequentially applying an electric field at a plurality of frequencies to a medium in a chamber, the medium comprising one or more particles (e.g., cells) suspended in a fluid; (ii) tracking the location of the one or more particles in the chamber while applying the AC electric field; (iii) calculating a velocity of each of the one or more tracked particles at each electric field frequency from the locations; and (iv) determining a characteristic of the one or more particles from the calculated velocities.

Embodiments of the method can include one or more of the following features and/or features of other aspects.

The method can include measuring a size of each of the one or more particles. Measuring the size of each of the one or more particles can include acquiring an image of the one or more particles in the chamber and determining the sizes from the image. Determining the sizes from the image can include determining a figure of merit for a particle in the image. Determining the sizes from the image can further include optimizing the figure of merit.

Tracking the location of the one or more particles can include acquiring a series of images of the one or more particles at each frequency. Tracking the location can include identifying the one or more particles in the series of images at a frequency.

Calculating the velocity of a particle can include normalizing the velocity based on the size of the particle. In some embodiments, calculating the velocity of a particle includes normalizing the velocity based on the location of the particle. Alternatively, or additionally, calculating the velocity of a particle can include normalizing the velocity based on the electric field strength at the particle's location. The electric field strength is determined using a computer model (e.g., a computer model that accounts for a finite thickness of the electrode elements).

Calculating the velocity of a particle can include normalizing the velocity based on the electric field gradient at the particle's location. The electric field gradient can also be determined using a computer model.

Determining the characteristic of the one or more particles can include determining the dielectrophoretic cross-over frequency for the particles. Determining the dielectrophoretic cross-over frequency for the one or more particles can include using a parametric fitting function that relates particle velocity to frequency. The parametric fitting function can include at least three fitting parameters.

Determining the characteristic of the one or more particles can include determining a frequency or range of frequencies where the one or more particles experience a maximum positive dielectrophoretic force. Calculating a velocity of each of the one or more particles can include calculating multiple velocity values of the velocity at the frequency or in the range of frequencies where the one or more particles experience a maximum positive dielectrophoretic force.

Determining the characteristic of the one or more particles can include determining a frequency or range of frequencies where the one or more particles experience a maximum negative dielectrophoretic force. Calculating a velocity of each of the one or more particles can include calculating multiple velocity values of the velocity at the frequency or in the range of frequencies where the one or more particles experience a maximum negative dielectrophoretic force.

The applied electric field can be generated by a waveform comprising sinusoidal waveform and/or by a digitally synthesized waveform.

The one or more particles can include particles that are labeled with a fluorescent moiety.

The method can further include treating the medium with a chemical or physical agent and determining an effect of the treatment on the characteristic of the one or more particles as a function time. Alternatively, or additionally, the method can include treating a surface adjacent the medium with an agent to modify the interaction of one or more of the particles with the surface. The agent can cause the surface to selectively adhere or repel one or more of the particles. The method can include determining an effect of the treatment on the characteristic of the one or more particles as a function of time.

The method can include identifying any of the one or more particles that form a pearl chain. The characteristic can be determined from particles that do not form a pearl chain.

In another aspect, the invention features a method, including: (i) sequentially applying an AC electric field at a plurality of frequencies to a medium in a chamber, the medium including a plurality of particles suspended in a fluid; (ii) measuring a velocity of each of the plurality of particles at each electric field frequency; and (iii) determining a dielectrophoretic cross-over frequency for the particles from the measured velocities.

Embodiments of the invention can include one or more of the features of other aspects.

In a further aspect, the invention features a method that includes: (i) sequentially applying an AC electric field at a plurality of frequencies to a medium in a chamber, the medium including a plurality of particles suspended in a fluid; (ii) acquiring a series of images of the plurality of particles at each frequency; (iii) measuring a velocity of each of the plurality of particles at each electric field frequency; and (iv) measuring a size of each of the plurality of particles.

Embodiments of the invention can include one or more of the following features and/or features of other aspects.

The method can include determining a cross-over frequency for the particles from the measured velocities.

Measuring the velocity of each of the plurality of particles can include monitoring positions of the plurality of particles in each of the series of images. Measuring the velocity of each particle can include determining the change in position of each particle in between images.

Determining a cross-over frequency for the plurality of particles can include determining an individual cross-over frequency for each of the plurality of particles and statistically analyzing the individual cross-over frequencies.

In yet a further aspect, the invention features a method, including: (i) sequentially applying an AC electric field at a plurality of frequencies to a medium in a chamber, the medium including a plurality of particles suspended in a fluid; (ii) electronically acquiring a series of images of the plurality of particles at each frequency; and (iii) determining a cross-over frequency for the particles from the images.

Embodiments of the invention can include one or more of the features of other aspects.

In another aspect, the invention features a method, including: (i)sequentially applying an AC electric field at a plurality of frequencies to a medium in a chamber, the medium including a plurality of particles suspended in a fluid; (ii) acquiring a series of images of the plurality of particles at each frequency; and (iii) determining a velocity for each particle from each series of images.

Embodiments of the invention can include one or more of the features of other aspects.

In another aspect, the invention features a system for performing dielectrophoretic analysis on a population of particles. The system includes a chamber having a wall, a plurality of electrodes disposed on the wall of the chamber, a function generator configured to supply an AC voltage to the plurality of electrodes, a detector configured to acquire images of a sample disposed in the chamber; and an electronic controller in electrical communication with the detector. During operation of the system, the function generator sequentially supplies an AC voltage to the plurality of electrodes at a plurality of frequencies while the detector acquires a series of images of a sample in a chamber, the sample including one or more particles (e.g., cells) suspended in a fluid, and the electronic controller tracks the location of the one or more particles in the chamber, calculates a velocity of each of the one or more particles at each electric field frequency from the tracked locations, and determines a characteristic of the one or more particles from the calculated velocities.

Embodiments of the invention can include one or more of the following features and/or features of other aspects.

The system can include an optical microscope positioned relative to the chamber to image the sample to an image plane. The detector can be positioned at the image plane.

The electrodes can include polynomial electrodes and/or interdigitated electrodes.

In some embodiments, the plurality of electrodes includes an array of electrode regions. The array of electrode regions can include an 8×12 array of electrode regions (e.g., configured for use with a 96-well plate).

Embodiments of the invention may include one or more of the following advantages.

Embodiments can enable rapid and/or accurate measurement of physical properties (e.g., DEP cross-over frequency and particle size) of a particle or population of particles. Due to speed and accuracy of measurements, embodiments can be used to investigate the DEP properties of large numbers of particles in a single cycle of the DEP apparatus (e.g., a sufficiently large number of particles to reduce statistical variance to useful levels). For example, in some embodiments, the DEP cross-over frequency can be determined for a population of about 50 particles in one experimental run lasting less than two minutes. In some embodiments, the DEP characteristics of 1000 or more particles can be determined in one experimental run of less than two minutes. Furthermore, because large numbers of particles can be rapidly characterized, particle parameters can be determined with greater statistical accuracy, and for biological particles errors associated with biological variability can be minimized.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

Figure 1:
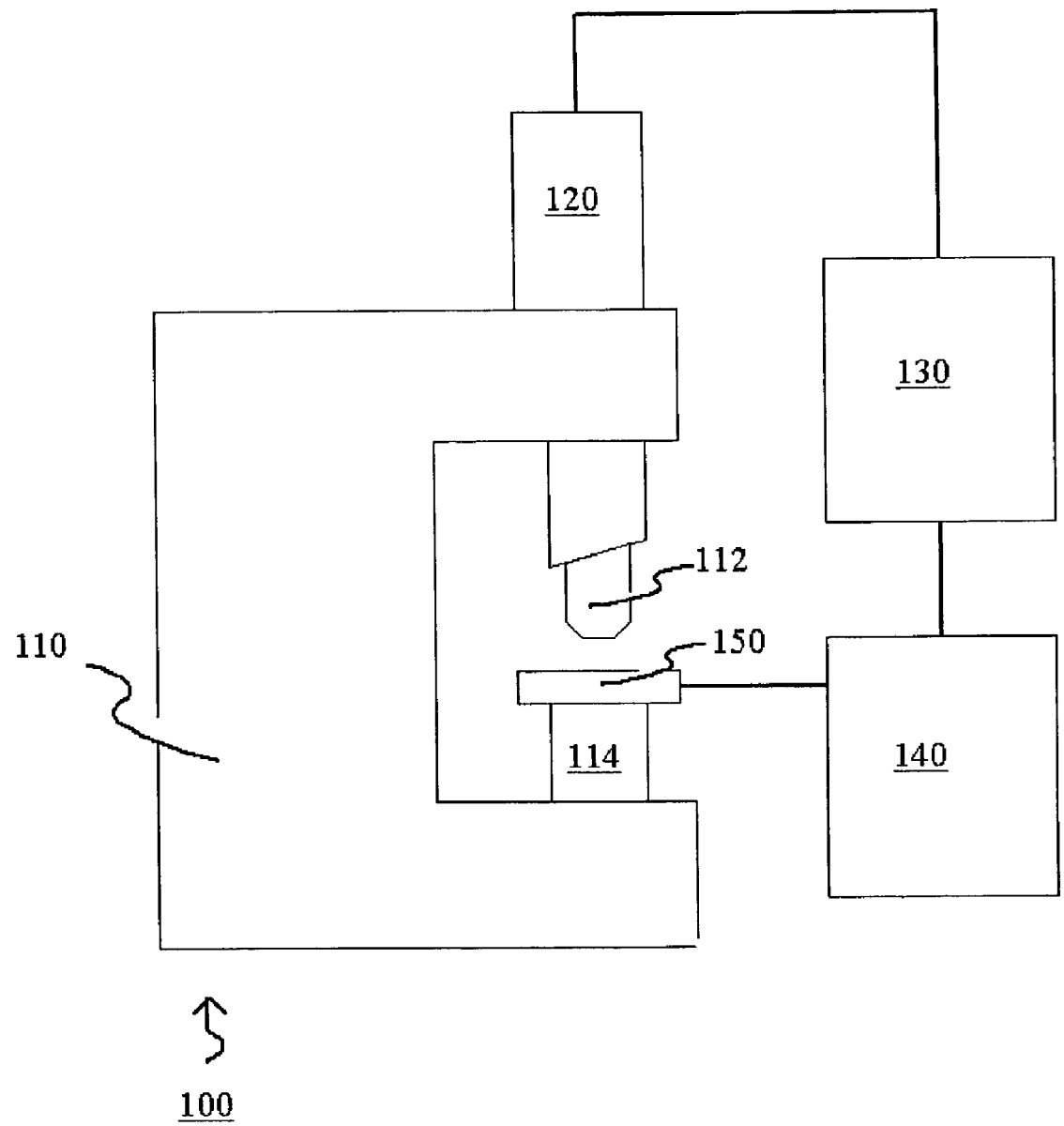
FIG. 1 is a schematic diagram showing an embodiment of a dielectrophoresis system.

Referring to FIG. 1, the effect of an applied electric field on a suspension of particles in a fluid is studied using a dielectrophoresis (DEP) system 100. DEP system 100 includes an optical microscope 110, which images the particles onto a CCD camera 120. The output of CCD camera 120 is connected to a PC computer 130. The particles are confined to a DEP electrode apparatus 150, which is positioned on microscope stage 114 relative to the optical microscope's objective lens 112. The output of a function generator 140 is connected to an electrode array in DEP electrode apparatus 150. DEP electrode apparatus is also connected to PC computer 130 via a function generator 140 so that the PC can control the application of signals to electrode apparatus 150. This connection allows PC computer 130 to monitor particle activity at electrodes in DEP electrode apparatus.

During operation of the DEP system, function generator 140 applies an AC voltage to microelectrodes in DEP electrode apparatus 150, generating a spatially non-uniform electric field in the fluid. The electric field, when applied at certain frequencies, causes the particles in the fluid to move. An image capture card installed in PC computer 130 acquires images from CCD camera 120. PC computer 130 stores and analyzes the acquired images.

The image capture card and CCD camera 120 can be selected to provide a suitable image acquisition rate. A suitable acquisition rate is sufficiently high that a particle's displacement between successive frames under the influence of a dielectrophoretic force is sufficiently small that a particle can be tracked from one frame to the next. A frame rate suitable for many applications is about 10 Hz, although the frame rate can be slower (e.g., about 1 Hz or slower) or higher (e.g., about 100 Hz or higher). The higher frame rates could be used, for example, to monitor rapid cell physiology events, such as changes in membrane ion channel activity after exposure to a chemical agent (e.g., events that take place over milliseconds or tens of milliseconds).

Figure 2:
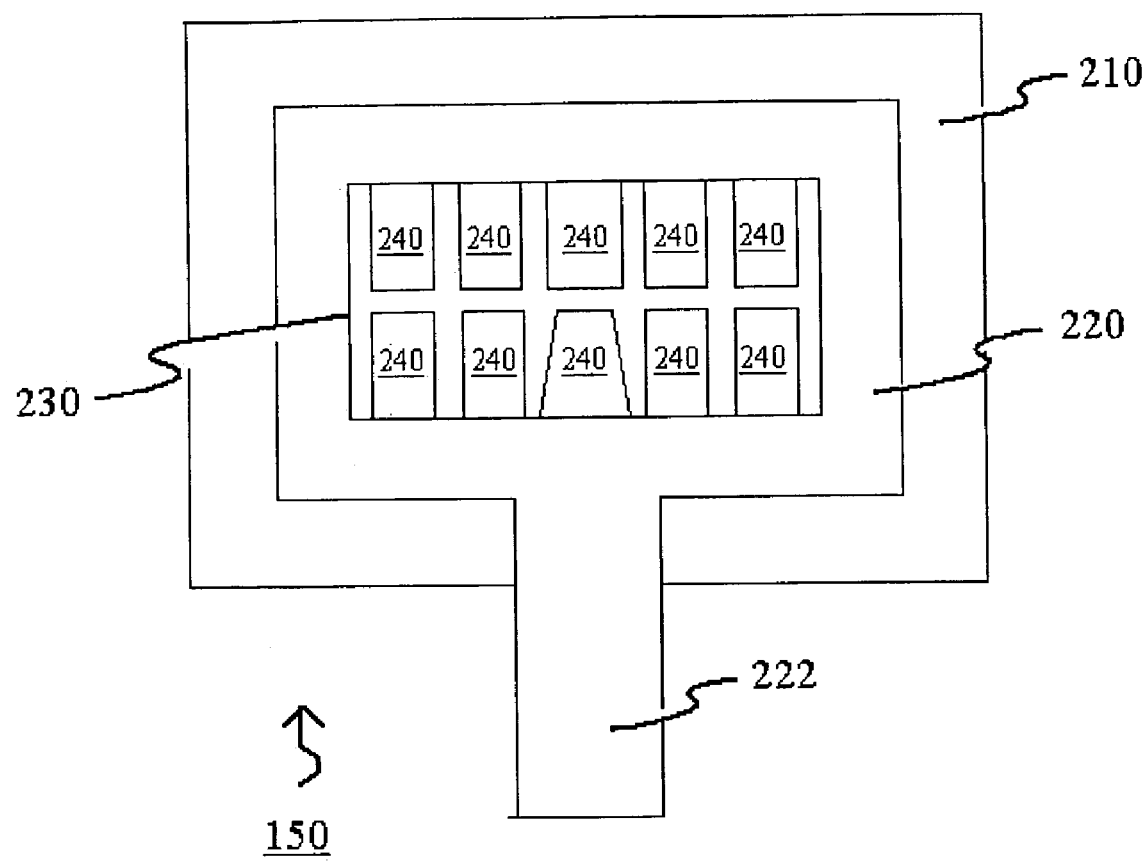
FIG. 2 is a plan view of an electrode apparatus used in the dielectrophoresis system shown in FIG. 1.

Referring to FIG. 2, DEP electrode apparatus includes an electrode driving board 210, which includes connectors for interfacing with the function generator. Electrode driving board 210 supports an electrode loading tray 220 and an electrode array 230. Electrode loading tray 220 facilitates easily loading of electrode array 230 into and out of DEP electrode apparatus 150. Electrode array 230 includes several electrode regions 240 supported by a transparent substrate. Each of the electrode regions includes one or more electrodes. The electrodes are designed to provide a desired electric field profile to the fluid between the electrodes when a voltage is applied to the electrodes.

Electrode array 230 can be fabricated using photolithographic techniques. The electrodes are etched from a layer of a conductive material disposed on a transparent substrate (e.g., a glass substrate). The conductive material can be transparent (e.g., indium tin oxide) or opaque (e.g., gold or chromium).

In the described embodiment, electrode array 230 is covered by a removable coverslip. Electrode array 230 and the coverslip form a chamber, which substantially confines the fluid and particles to a region of the electrode array 230 proximate to electrode regions 240. Typically, a user pipettes the fluid and particles onto the top surface of electrode array 230 and then covers the exposed suspension with the coverslip to form the chamber.

Figure 3A:
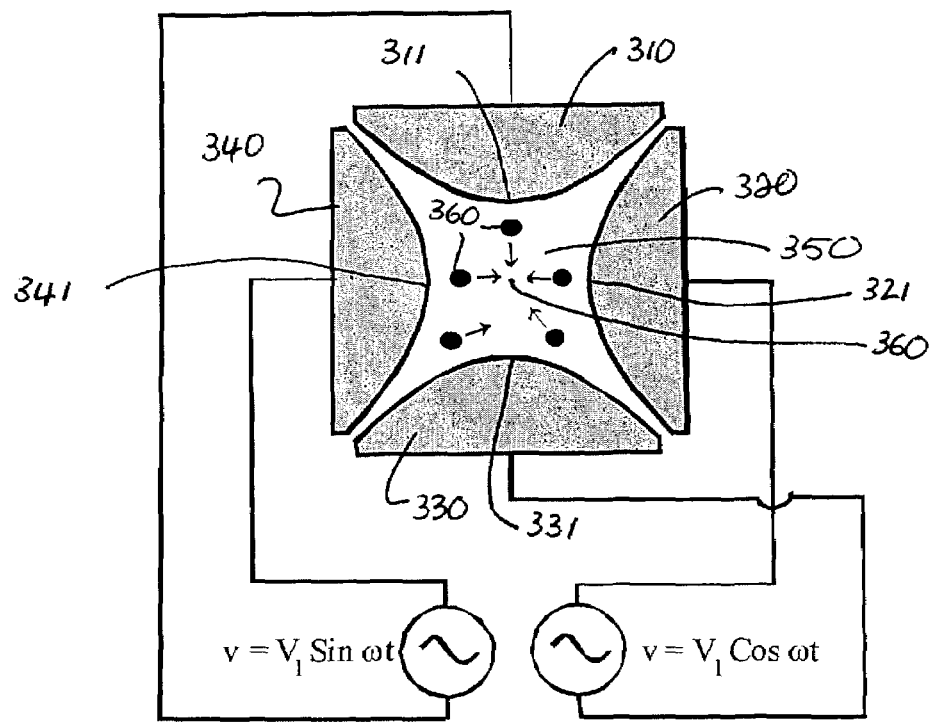
FIG. 3(*a*) and FIG. 3(*b*) are schematic diagrams showing motion of particles under (a) a negative dielectrophoretic force, and (b) a positive dielectrophoretic force.
Figure 3B:
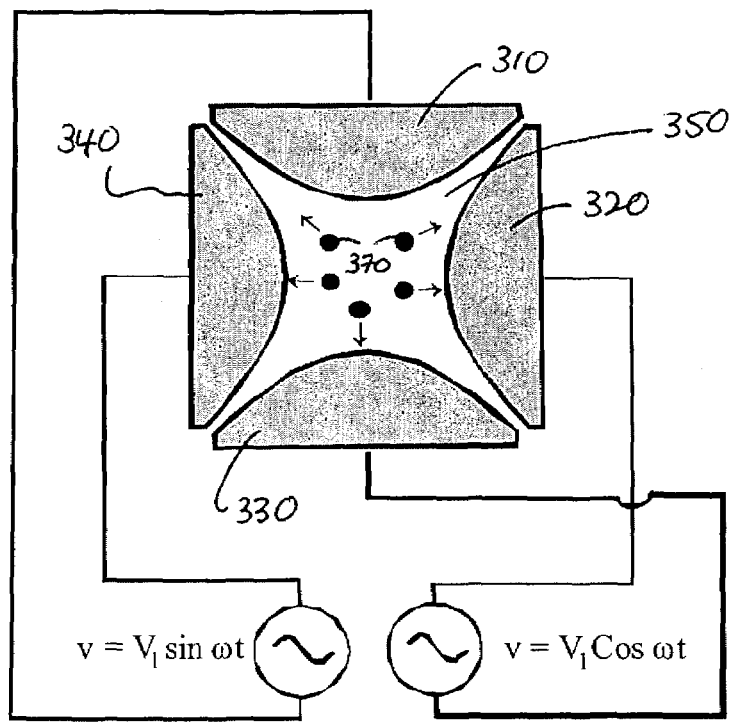

Referring to FIG. 3(*a*) and FIG. 3(*b*), an electrode region includes four electrode elements 310, 320, 330, and 340. The electrode elements are separated by an electrically insulated region 350. Center 360 of electrically insulated area 350 is defined as the point equidistant from electrode element tips 311, 321, 331, and 341. Each electrode element pair located opposite insulated region 350 is connected to a voltage source. In other words, electrode elements 310 and 330 are connected to one voltage source, and electrode elements 320 and 340 are connected to another voltage source. Particles 370 are suspended in the fluid adjacent insulated region 350.

Electrode elements 310, 320, 330, and 340 form polynomial electrodes. As used herein, polynomial electrodes refer to electrodes designed on the assumption that the electrical potential at any point created by an electrode system of interest is defined by a polynomial that obeys Laplace's equation. By substituting this polynomial into Laplace's equation the corresponding equipotentials can therefore be determined, and these in turn can be used to define the electrode boundaries. During operation, a first AC potential difference is applied across electrode electrodes 310 and 340 (indicated as $V_1 \sin(\omega t)$ in FIGS. 3(*a*) and 3(*b*)), and another AC potential difference is applied across electrode elements 320 and 330 (indicated as $V_1 \cos(\omega t)$ in FIGS. 3(*a*) and 3(*b*)). The two potentials have same frequency and amplitude but are 90 degrees out of phase. The potential difference between the electrodes generates an electric field in the fluid adjacent insulated region 350. Depending on the AC frequency and field strength, particles 370 can move in response to the electric field. Referring specifically to FIG. 3(*a*), for some frequencies, the particles can move away from electrode elements 310, 320, 330, and 340. In such cases, particles 370 motion is caused by negative dielectrophoresis. Referring now to FIG. 3(*b*), at other frequencies, particles 370 can move towards the electrode elements. This motion is caused by positive dielectrophoresis.

The amplitude of the applied voltage can be varied as desired. Typically, a voltage of sufficient amplitude to induce an observable dielectrophoretic response under investigation is applied to the electrodes at a given sample rate for the image capture card. For example, for electrode geometries where opposite electrode tips are separated by 0.5 millimeters, a voltage of about five volts peak-to-peak is sufficient for many particles.

Typically, the applied AC voltage is a sinusoidally-varying voltage, although other pulse shapes can be employed. Examples of other pulse shapes include square-wave pulse shapes and saw tooth pulse shapes. In some embodiments, the applied voltage can be the superposition of multiple sinusoidally-varying voltage waveforms. The frequency and/or amplitude of the sinusoidal waveforms can be the same or different. One example of an applied voltage formed from a superposition of multiple sinusoidally-varying waveforms is a voltage formed from a waveform having frequency ω and waveforms having harmonic frequencies (e.g., 2ω, 3ω, 4ω, . . . ). In some embodiments, system 100 can include a waveform synthesizer, and the applied voltage can be formed by digitally synthesizing a desired waveform. The applied voltage waveform can vary as desired during data acquisition. Where the waveform is non-sinusoidal, the frequency refers to the number of times the waveform repeats itself per unit time.

The AC frequency may be varied as desired while images of the particles are acquired. In some embodiments, personal computer 130 will cause function generator 140 to sequentially scan through a range of frequencies while acquiring images from CCD camera 120 at a number of frequencies within the range. Several images (e.g., 100 or more) are acquired for each of the frequencies.

In general, the range of frequencies scanned and the increment between successive frequencies depends on the sample being investigated. For example, for a population of blood cells, the frequency range scanned can be from about 0.1 MHz to 1 MHz in 0.1 MHz increments. For a population of plant cells, the corresponding frequency range can be from about 10 kHz to 0.1 MHz, and for a population of bacteria a frequency range extending from around 1 MHz to 10 MHz can be used. More generally, frequency ranges can extend from the Hz and kHz range (e.g., about 1,000 Hz, 100 Hz, 10 Hz or less) to the MHz range or greater (e.g., about 0.1 MHz, 1 MHz, 100 MHz or more). The increment between successive acquisition frequencies usually depends on the frequency range. The increment will typically be small enough to provide a sufficient number of data points within the frequency range, but sufficiently large to scan the entire frequency range of interest. For example, where the range is small (e.g., 1,000 Hz) the increment will be small enough to provide sufficient data points in the range (e.g., 100 Hz increment providing 10 data points). Conversely, where the range is large (e.g., 1 MHz), the increment can be similarly large (e.g., 0.1 MHz).

The range of frequencies can be scanned linearly or non-linearly. During a linear scan, the increment between successive acquisition frequencies remains constant. During a non-linear scan, however, this increment can vary. An example of a non-linear frequency scan is one in which large increments are used to determine a sub-range of frequencies in which the particles exhibit some identifying behavior. Within this sub-range, the frequency increment is reduced to provide additional data points, which can more accurately characterize the particles.

In general, DEP system 100 can be used to study any dielectric particle that can be suspended in an appropriate fluid or medium.

In some embodiments, the particles may be biological particles. For example, the particles can be cells, or components of cells and/or microorganisms. Components of cells include proteins and DNA. Microorganism's include bacteria. Biological particles also include pathogens, such as viruses.

Particles can be polymeric. For example, the particles may include polystyrene microspheres.

Particles can be solid, semi-solid, liquid or gaseous. Solid particles include polymer spheres or protein macromolecules. Semi-solid particles include poly-acrylamide or agar gel particles. Liquid particles include the dispersed phase in an emulsion, such as oil droplets in water or liquid particles in an aerosol. Gaseous particles include the dispersed phase in a foam, such as gas bubbles in a liquid.

In some embodiments, particles can be tagged with a fluorescent moiety. Particles can be tagged for use with fluorescent microscopy techniques.

Particle size may vary. Typically, particles are large enough to be observed using optical microscopy (e.g., larger than about 0.5 microns in diameter, such as 1 micron or larger). In some embodiments, particles can be larger than about 1 millimeter in diameter. In some embodiments, however, particles may be used that are too small to be observed directly using optical microscopy. For example, a sample may consist of protein or virus particles that have been fluorescently labeled to aid detection by optical microscopy.

A sample can include one type of particle, or a mixture of particles. For example, a sample may be a mixture such as a blood sample, including red and white blood cells, platelets, in addition to other types of particle. An example of a single particle sample is a colloidal dispersion of polystyrene spheres in deionized water.

The number of particles in a sample may vary. In some embodiments, a sample may include a sufficiently large number of particles to take account of biological or natural variability of their size or properties. For example, a sample may include more than 10 particles (e.g., more than about 20 particles, 50 particles, 100 particles, 1000 particles).

Data Acquisition and Analysis

Figure 4:
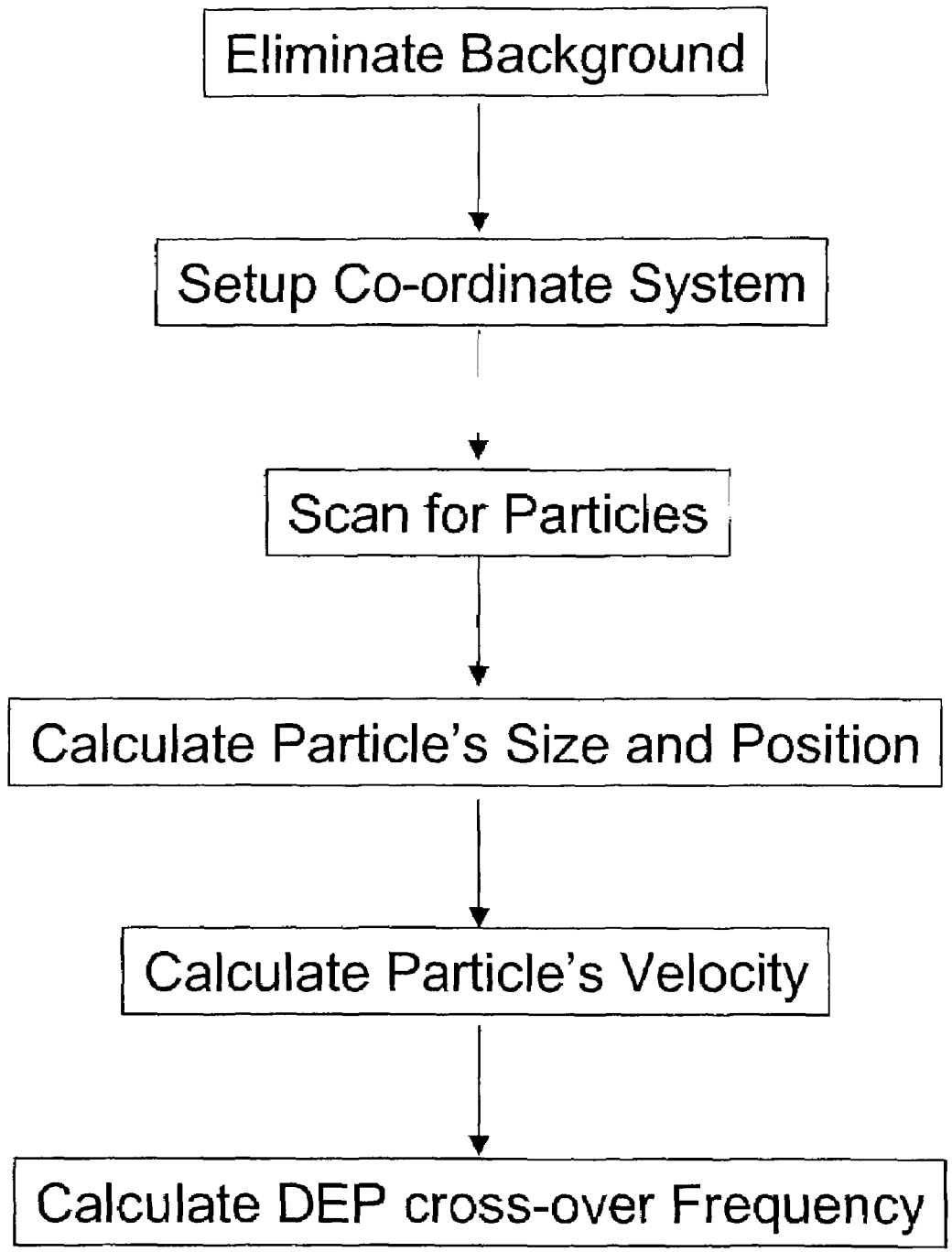
FIG. 4 is a flowchart of an algorithm used to analyze images acquired using a DEP system.

After PC controller 130 has acquired a series of images (also referred to as frames), it implements a software algorithm which identifies the particles in each frame, tracks the particles from frame to frame, determines the particles velocities at each applied frequency, and computes the particles' DEP cross-over frequency. The DEP cross-over frequency is the frequency which, when applied to the electrodes, produces no net force on the particle under consideration. The algorithm is summarized in the flow chart shown in FIG. 4.

As a first step in the analysis, the algorithm eliminates background pixels from each frame. Depending on the number of particles in the frame, many pixels in each image can belong to one of two sets, a low light intensity set corresponding to the electrodes, or a high light intensity set corresponding to the electrically insulated region between the electrodes. Because the particles usually correspond to intermediate intensity pixels, these low intensity pixels and high intensity images can be excluded from further analysis. Excluding these pixels can speed up the algorithm.

To eliminate background pixels, the algorithm first takes an intensity histogram of the entire image. Each pixel has 24 bit color depth (i.e., red, green, and blue sub-pixels each having eight bit gray scale). Accordingly, each sub-pixel has an intensity value from 0 to 255. The intensity of each pixel is computed by averaging the red/green/blue values. A histogram array with 256 bins is then used to create an intensity histogram of the entire image. Typically, this histogram has two distinct peaks, which are identified using a windowing technique on the 1D histogram array. The low-intensity peak corresponds to pixels imaging the electrode, and a high-intensity peak corresponds to pixels imaging the electrically insulated region. All pixels in the image that fall below a low intensity threshold (e.g., corresponding to the highest intensity pixel corresponding to an electrode) are assigned a first intensity value (e.g., 0). Those pixels having intensity above a high-intensity threshold (e.g., corresponding to the lowest intensity pixel corresponding to the electrically insulated region) are assigned a second intensity value (e.g., 255).

The next step in the analysis is to setup a coordinate system within which particles can be tracked from frame-to-frame.

A particle's position is defined by the distance from the center of the particle to a user specified origin (e.g., center 360 of electrically insulated area 350). Referring again to FIGS. 3(*a*) and 3(*b*), in the described embodiment, which has a polynomial electrode geometry, the velocity of a given particle is expected to be proportional to the time-dependent distance between that particle and center 360 of electrically insulated area 350. Hence, the algorithm determines the pixel coordinate of center 360 of electrically insulated area 350.

In order to determine the pixel coordinate of center 360, the algorithm determines pixel coordinates of tips 311, 321, 331, and 341 of electrode elements 310, 320, 330, and 340, respectively. For the tip 341, the algorithm starts out at the center vertical pixel on the left side of the image and looks for transition from the second intensity value to the first intensity value (e.g., from 0 to 255). The last pixel having the second intensity value is defined as the left side of the circle. A similar procedure is used to find tips 311, 321, and 331. Once the tips have been located, the center of the coordinate system is defined as the average of the location of the left and right tips (i.e., tip 341 and tip 321, respectively) for the horizontal coordinate and the average of the top and bottom tips (i.e., tip 311 and tip 321, respectively) for the vertical coordinate.

After setting up a coordinate system, the algorithm proceeds to scan each frame for particles. The algorithm can restrict the search to an area inside of the electrodes, and can ignore the background in this region. Accordingly, the algorithm identifies individual particles within an area of interest and provides a rough estimate of the size and position of these particles.

The algorithm finds particles by scanning the frame column-by-column and identifying pixels that have an intensity value different from the background intensity (e.g., background pixels that have previously been assigned the first intensity value). When the algorithm finds a pixel that has an intensity value different from the background intensity value, the algorithm looks for adjacent pixels that also have intensities different from the background. Accordingly, the algorithm identifies sets of adjacent pixels. If a set matches certain criterion (e.g., number of pixels, vertical and horizontal range of the set), then this set of pixels is determined to be a particle. The size and position of the cell may also be roughly determined by the size of and position of the set of adjacent pixels.

After identifying particles, the algorithm determines the size and position of each identified particle. In this step, the algorithm uses the previously determined rough estimate of the center and size of each particle to more accurately determine the center and size of each particle.

Figure 5:
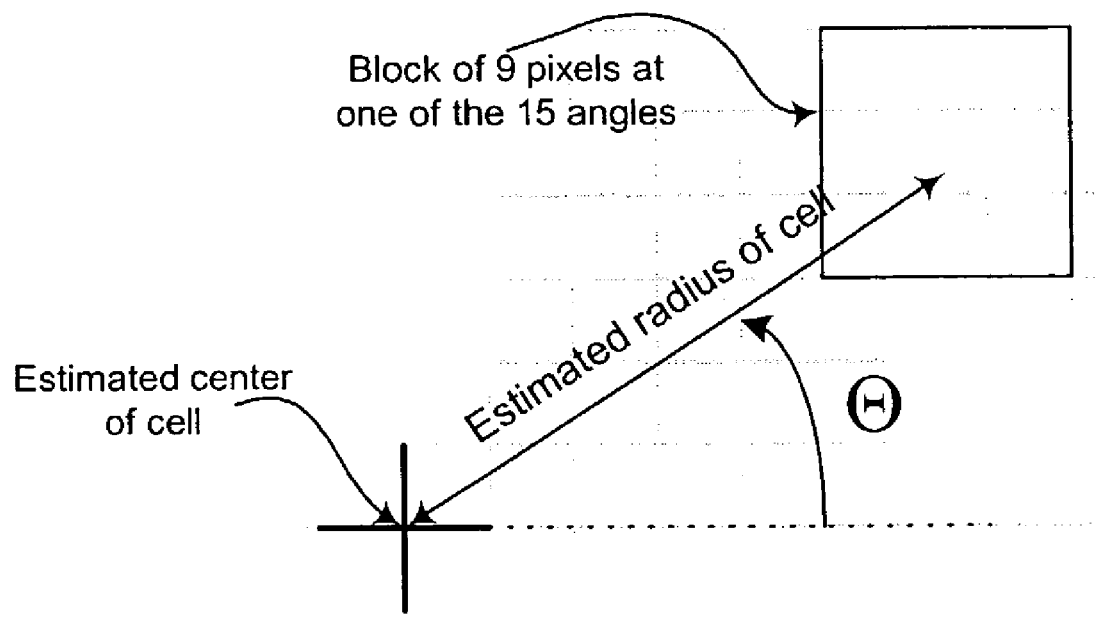
FIG. 5 is a schematic diagram showing pixels used to determine a figure of merit for the radius of a particle.

To more accurately determine the location and size of each particle, the algorithm fits a predetermined shape (e.g., a circle, an ellipse, or a polygon, such as a square or hexagon) to each particle. For example, where the particles are cells, the algorithm can fit a circle to the dark part (i.e., low intensity) of an image of each cell's membrane. Typically, the image of the cell includes three concentric circular regions, a dark circle sandwiched between two lighter circles. Referring to FIG. 5, starting with an estimate of the center of the cell and of its radius, the algorithm identifies the intensity of pixels corresponding to a set of pixels at a series of different azimuthal angles, $\Theta$, measured from a horizontal axis originating at the estimated center of the cell.

For example, 15 sections can be studied at equal angular increments around the cell image. For each section, the algorithm determines an overall figure of merit for a cell image, according to the intensity of the nearest neighbor pixels to the pixel located the estimated cell radius away from the estimated cell center. The overall figure of merit is derived from the addition of two parameters. The first parameter quantifies the darkness of the cell membrane at the edge of the fitted shape. The larger this first parameter is, the more distinct the cell image. This first parameter rapidly reduces in magnitude for cells that become out of focus or have a physically disrupted membrane (e.g., after bursting). The second parameter quantifies the uniformity of the membrane darkness around the cell perimeter. The smaller this second parameter, the more non-uniform is the cell membrane. This second parameter is sensitive to very uneven, discontinuous or oddly shaped cell membranes.

In order to find the optimum center coordinate and cell radius, the center coordinate and cell radius are modified slightly (e.g., by moving a pixel in the horizontal and/or vertical direction) and the two figure of merit parameters are computed again. For each set of center coordinate values and cell radii, the algorithm determines a figure of merit sum for the cell. In an iterative procedure, the algorithm modifies one or more of the estimated vertical position of the cell; the estimated horizontal position of the cell; and/or the estimated radius of the cell. Changes in one of these parameters that increase the figure of merit sum for all positions are rewarded by continuing to change that parameter in the direction that increased fitness. When further changes to any of the three parameters fail to yield increases in fitness, then the iteration cycle is complete, and the final estimate of the cell center position and radius are taken as the cell center position and cell radius for that frame.

In general, the figure of merit and predetermined shape used to determine the figure of merit are selected according to the type of particle being studied. For example, while the above description refers specifically to a figure of merit and shape (i.e., circle) for when the particles being studied are cells, other shapes and figures of merit may be used.

These sets are usually performed for each frame acquired during the experiment. The resulting data includes the position (e.g., an x, y coordinate) and size (e.g., radius) of each particle with respect to the coordinate system for each frame. It may be desirable to run the aforementioned steps more than once for the first frame (or first few frames) in an experiment in order to obtain initial estimates of the position of each cell.

Next, the algorithm calculates each particle's velocity for a series of frames. Typically, a series of frames corresponds to frames acquired for a particular frequency. Accordingly, by performing this analysis for each acquisition frequency, the analysis provides a particle velocity as a function of applied field frequency.

In general, a particle's velocity is determined from the displacement of the particle's center position between different frames, and the time increment between successive frame acquisitions. The velocity is computed by creating a particle tracking file that appends the tracked particle position and size for each particle in each frame using the previously described algorithm and then comparing the change in position corresponding to the frame rate. The velocity can be expressed in terms of pixels per second, or, where the apparatus is calibrated and the imaged area known, velocity can be expressed as, e.g., microns per second.

Figure 6:
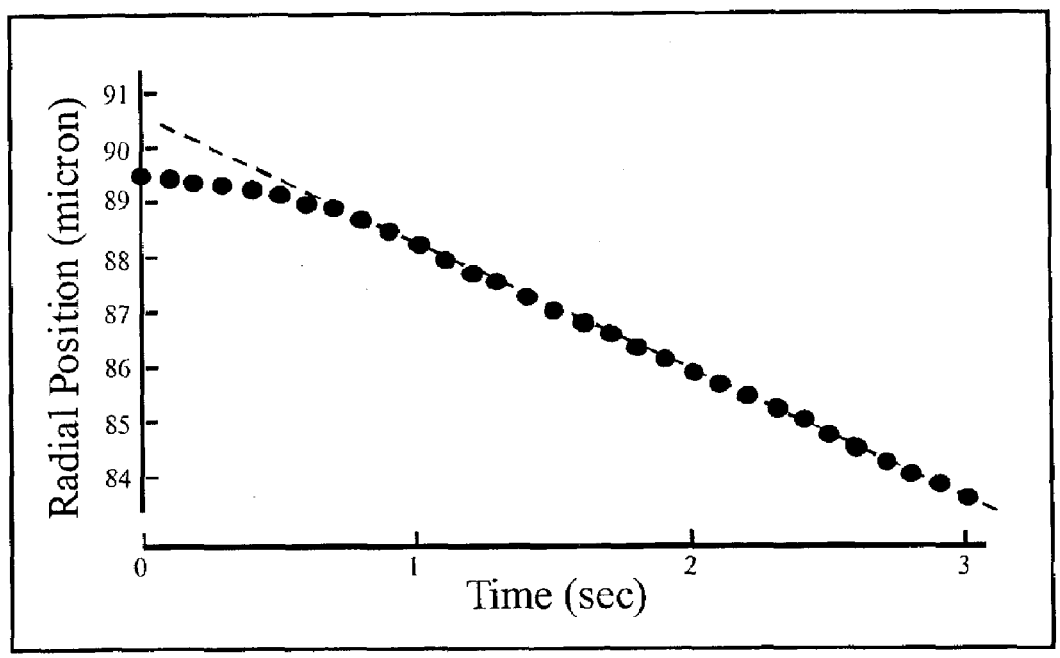
FIG. 6 is a plot showing a particle's position as a function of time while under the influence of a negative dielectrophoretic force.

Referring to FIG. 6, a particle's dynamic response can be determined by studying its position as a function of time. In this example, the particle's position is determined as its radial distance from center 360. At the applied frequency for this example, the particle experiences negative DEP force and moves toward center 360. Starting from rest at 0 seconds, the particle accelerates in the first second under the influence of the dielectrophoretic force and reaches a steady-state velocity after about one second. The particle's velocity is determined by performing a linear regression on this data, ignoring those data points acquired in the first second while the particle is accelerating.

In general, a velocity is determined for one or more particles at each applied frequency. The frames used to compute each particle's velocity at a frequency can be a subset of the frames acquired at that frequency. For example, frames acquired while the particle is not at a steady-state velocity can be ignored while determining particle velocity.

The algorithm also adjusts the velocity to compensate for the electrode geometry. For example, for the polynomial electrode shape described above, the velocity is adjusted by multiplying by a factor of (1/R), where R is the radial position of the particle center in each frame. This compensation normalizes the particle velocities to account for variations in the electric field strength and/or gradient, which are both dependant on the particles position with respect to the electrode.

More generally, the velocity of each particle can be normalized with respect to variations of the electric field strength and electric field gradient between the electrode edges. For the purposes of this compensation, the electric field profile for a particular electrode geometry can be determined by computer modeling. An example of computer software that can be used to model the electric field profile for different electrode geometries is Maxwell 3D Electromagnetic Field Simulator from Ansoft (Pittsburgh, Pa.). In preferred embodiments, the electric field profile is modeled accounting for the three-dimensional nature of the electrodes. In other words, the model accounts for the finite thickness of the electrodes.

Under the influence of a dielectrophoretic force, a particle reaches its steady-state velocity when the dielectrophoretic force accelerating the particle is balanced by the viscous force of the fluid resisting the acceleration. Because both viscous force and the dielectrophoretic force depend on the particle size, particle velocity also depends on particle size. Accordingly, in some embodiments, the particle velocities can also be normalized with respect to each particle's size.

Once the particles velocities are known for each frequency, the algorithm determines the DEP cross-over frequency for each particle. The DEP cross-over frequency is computed using velocity values for a given particle over a range of frequencies. In order for the algorithm to function reliably, there should be at least one measurement (preferably several) at a frequency that provides a negative dielectrophoretic response for the particles well below the DEP cross-over frequency (e.g., for many cells suspended in an aqueous medium of conductivity of around 40 mS/m, a 20 kHz frequency is sufficiently low) and at least one measurement (preferably several) at a frequency that provides a positive dielectrophoretic response well above the DEP cross-over frequency (e.g., 500 kHz for most cells in a suspending medium conductivity around 40 mS/m).

In some cases, some particles attract each other to form particle chains. Such particle chains are often referred to as "pearl chains" and the phenomenon is referred to as "pearl chaining", which is described in detail in *Electromechanics of Particles*, by T. B. Jones, Ch. 6 & 7, Cambridge University Press (1995). The response of particles in pearl chains to an applied electric field can be different from free particles (i.e., particles that have not formed pearl chains). Accordingly, it can be advantageous to eliminate data corresponding to pearl chains from subsequent analysis.

System 100 can analyze how the DEP cross-over frequency of a particle is altered as a result of it interacting with other particles to form pearl chains. This is achieved by monitoring the separation distance between tracked particles. The user can define a minimum separation distance between adjacent tracked cells. When two particles are closer than this minimum separation distance, the particles are identified as a pearl chain composed of two particles, and the reported DEP cross-over frequency is reported separately from the data for single particles to allow for separate analysis. Multiples of particles attached together in pearl chains are similarly reported, with an indication of the number of particles tracked as part of that chain.

To link the data acquired in the above-described analysis with physical and or physico-chemical properties of the particles, it can be useful to link the data to particle parameters used in a theoretical DEP model. In particular, where the particles are cells, the time averaged DEP force $<F(t)>$ acting on a cell can be described using the Maxwell stress tensor formulation [see, e.g., Sauer, F. A., in: Chiabrera, A., Nicolini, C., Schwan, H. P. (Eds.) *Interactions between Electromagnetic Fields and Cells*, Plenum Publ. Corp. 1985, 181–202.], but for the common case, where dielectric losses are not too high, a more computationally convenient equivalent dipole moment formulation can be used. In this case, the force acting on a particle in a field of magnitude E and gradient $\nabla E$, is given by:

$$<F(t)> = Re\{m(\omega)\}\nabla E^2/2E \qquad (1)$$

where Re denotes the real (in phase) component of the dipole moment, $m(\omega)$, induced in the cell. The induced dipole moment varies with the radian frequency $\omega$ of the applied field, according to the relationship:

$$m(\omega) = 4\pi\epsilon_m r^3 f(\epsilon^*_p, \epsilon^*_m) E \qquad (2)$$

where r is the cell radius and $f(\epsilon^*_p, \epsilon^*_m)$ is the Clausius-Mossotti factor defined as $$f(\epsilon^*_p, \epsilon^*_m) = (\epsilon^*_p - \epsilon^*_m)/(\epsilon^*_p + 2\epsilon^*_m) \qquad (3)$$

The factors $\epsilon^*_p$ and $\epsilon^*_m$ are the particle and suspending medium complex permittivities, respectively, defined by $\epsilon^* = \epsilon - j(\sigma/\omega)$ with $\epsilon$ the permittivity, $\sigma$ the conductivity and $j=\sqrt{-1}$.

From equations 1–3, the DEP force is given by:

$$<F(t)> = 2\pi r^3 \epsilon_m \alpha (\nabla E^2) \qquad (4)$$

where $\alpha$ is the real component of the Clausius-Mossotti factor defined by equation 3, and which theoretically can have a value ranging from –0.5 to +1.0.

At the $DEP_{xo}$ frequency, the induced dipole moment is zero. In other words, at this frequency, the cell appears to be transparent to the applied field, and no charges are induced on or within the cell. The value for the DEP cross-over frequency, $DEP_{fxo}$, is determined theoretically from following equation:

$$DEP_{fxo} = \frac{1}{2\pi} \sqrt{\frac{(\sigma_m - \sigma_p)(\sigma_p + 2\sigma_m)}{(\varepsilon_p - \varepsilon_m)(\varepsilon_p + 2\varepsilon_m)}} \quad (5)$$

The algorthim then proceeds to fit a curve to the velocity vs. frequency data using a three parameter model derived as follows. Using a one shell model for a particle, the real component of the Clausius Mossotti can be expressed in terms of the conductivities, $\sigma_p$ and $\sigma_m$, and permittivities, $\varepsilon_p$ and $\varepsilon_m$, of the particle and medium, respectively, as:

$$\alpha = \frac{(\sigma_p - \sigma_m)}{(1 + \omega^2 \tau^2)(\sigma_p + 2\sigma_m)} + \frac{\omega^2 \tau^2 (\varepsilon_p - \varepsilon_m)}{(1 + \omega^2 \tau^2)(\varepsilon_p + 2\varepsilon_m)}, \quad (6)$$

where $\tau$ represents the characteristic Maxwell-Wagner relaxation time describing the polarization (charge accumulation) that occurs at the interface between the particle and its surrounding suspending medium for low volume fractions of suspended particles. By defining $$K_1 \equiv (\sigma_p - \sigma_m), \quad (7)$$
$$K_2 \equiv (2\pi)^2 \tau^2,$$
$$K_3 \equiv (\varepsilon_p - \varepsilon_m),$$

equation 6 becomes $$\alpha = \frac{K_1}{1 + \omega^2 K_2} + \frac{K_2 K_3 \omega^2}{1 + \omega^2 K_2}. \quad (8)$$

Expressing this in terms of $(1+\omega^2 K_2)$, equation 8 becomes $$\alpha = \frac{K_1 \left(1 + \frac{K_2 K_3}{K_1} \omega^2\right)}{1 + \omega^2 K_2}. \quad (9)$$

Redefining the parameters $K_1$, $K_2$, and $K_3$, by $$A = K_1, \quad (10)$$
$$B = \frac{K_2 K_3}{K_1},$$
$$C = K_2,$$

equation 9 can be rewritten as $$\alpha = A \frac{(1 + B\omega^2)}{(1 + C\omega^2)}. \quad (11)$$

Figure 7:
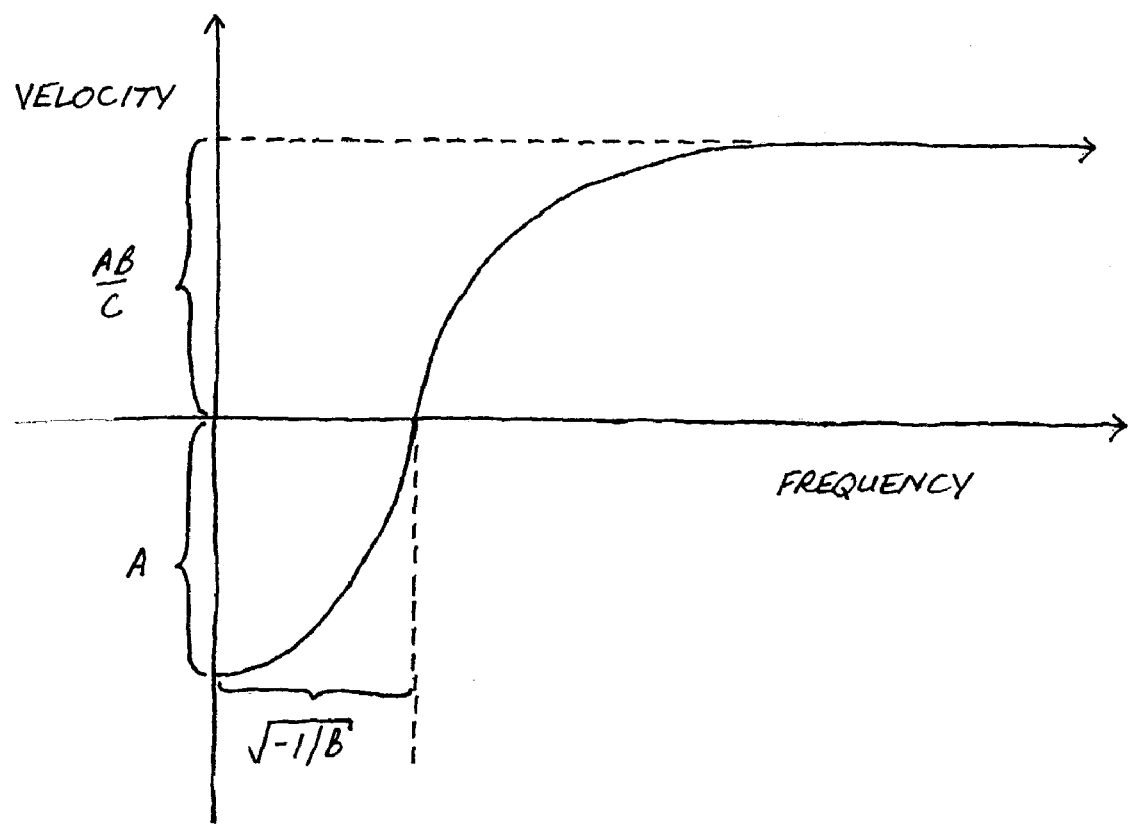
FIG. 7 is a plot showing a curve fitted to velocity/frequency data according to a three parameter fitting function.

Note that where $\omega^2$ is much smaller than B and C, then equation 11 reduces to approximately A. The algorithm fits a curve of the form given in equation 11 to the velocity vs. frequency data, optimizing the fit with the parameters A, B, and C. Referring to FIG. 7, A is shown by the low point on the velocity vs. frequency curve. At high frequency, where $\omega^2$ is much larger than B and C, equation 11 reduces to approximately AB/C, which is also shown in FIG. 7. At the cross-over frequency, equation 11 is equal to zero. This is satisfied where $1+B\omega^2=0$. Thus, B is negative and the cross over frequency is given by:

$$DEP_{fxo} = \sqrt{-1/B}. \quad (12)$$

Accordingly, the DEP cross-over frequency is given by the fitting parameter equation 12 and the fitting parameter B.

Applications

DEP system 100 can be used to determine the DEP response of particles under varying chemical and/or physical conditions. Knowledge of a particle's DEP response can be used for variety of purposes, including, for example, characterizing the properties of specific particle types, analyzing sub-populations of particles in particle mixtures, and/or analyzing the behavior in response to exposure to different chemical and/or physical agents.

In some embodiments, DEP system 100 can be used to study the response of a population of cells to a chemical agent. For example, DEP system 100 can be used as a tool to follow physiological changes in a cell membrane that accompany transmembrane signaling events (e.g., to study human T lymphocytes stimulated using phorbol myristate acetate and ionomycin). Changes in the DEP response (e.g., changes in the DEP cross-over frequency) of such cells after activation can be correlated to changes in the cells' membrane topography (e.g., reduction of membrane associated microvilli, blebs, and/or folding) via a theoretical model. One example of a theoretical model, relating specific cell membrane capacitance and conductance per unit area of the cell membrane to the DEP cross-over frequency, is disclosed in Huang, Y., Wang, X.-B., Becker, F. F., Gascoyne, P. R. C., *Biochim. Biophys. Acta*, 1282, 76–84 (1996).

More generally, DEP system 100 can be used to identify agents that produce a specific response in a cell population for the purposes of drug discovery.

In some embodiments, DEP system 100 can be used to determine parameters that are appropriate for the separation and/or identification of a particular type of particle from other particles, or to differentiate between different types of particles present in the dispersion. DEP system 100 can be used to analyze components of a mixture of several particles.

DEP system 100 can also be used to determine particle adhesion to a substrate. Because the dielectrophoretic force on a particle can be determined by correlating the particle's position to the electric field profile, the amount of force required to dislodge the particle from a substrate can be determined when the particle starts to move. By modifying a substrate (e.g., by chemical and/or physical surface treatment), DEP system 100 can be used to monitor changes in a particle's interaction with the substrate as a result of the modification.

Alternative Embodiments

In general, injecting and/or releasing the fluid into and out of the chamber can be performed manually or can be automated. In the described embodiment, fluid is manually supplied to the chamber by the user. In other embodiments, fluid supply can be automated. For example, the chamber may include an inlet port and an exhaust port, for supplying sample fluid into and removing sample fluid from the chamber. Tubing is connected between a fluid supply to the chamber. A pump draws a predetermined volume of fluid from the fluid supply and supplies it to the chamber on demand. Once the fluid sample has been studied, the fluid sample is pumped out of the chamber through the exhaust port. Depending on the nature of the fluid samples being studied, the chamber can be flushed with a cleansing sample (e.g., deionized water) before the next fluid sample is introduced. In some embodiments, personal computer 130 can control the introduction and removal of fluid samples from the chamber.

In some embodiments, PC 130 can also be used to control the function generator. This can increase the level of automation in the system, because, once initiated, the system can scan the entire frequency range without additional user input.

Although the above-described embodiment includes four polynomial electrode elements, other numbers of electrode elements and/or other electrode geometries can also be used. In preferred embodiments, the sum of the phase difference between the voltage applied to adjacent electrodes should be $2\pi$. For example, in the described embodiment having four electrode elements, the phase difference between each adjacent element is $\pi/2$ radians. Similarly, for an electrode configuration having N electrode elements (e.g., N=2, 3, 4, 5, 6, 7, 8, 9, 10 or more), the phase difference between the voltage applied to adjacent electrodes should be $2\pi/N$ radians. In some embodiments, the voltage can be applied to the electrodes to produce a traveling wave electric field.

Figure 8:
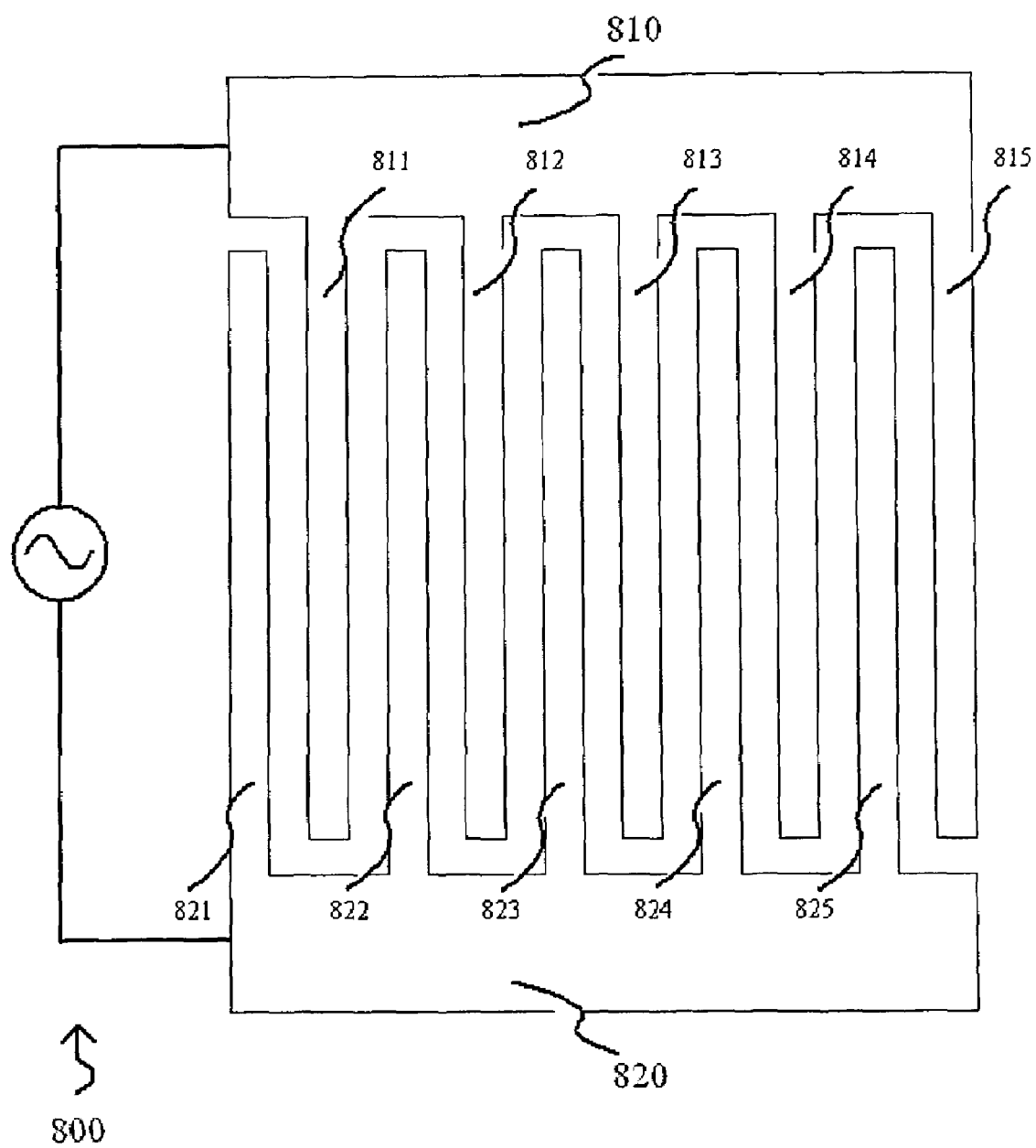
FIG. 8 is a schematic diagram showing interdigitated electrodes.

One example of an alternative electrode geometry is an interdigitated electrode geometry. Referring to FIG. 8, interdigitated electrodes 800 includes 10 parallel electrode elements. Electrode elements 811, 812, 813, 814, and 815 are in electrical contact to a first bus line 810, while electrode elements 821, 822, 823, 824, and 825 are in electrical contact to bus line 820. During operation, a power source applies an AC voltage between bus line 810 and bus line 820. Accordingly, the potential difference between electrode elements 811–815 and 821–825 gives rise to an electric field between the electrodes.

The dimensions of the interdigitated electrode elements can be varied as desired. In some embodiments, the electrodes are about five or more microns wide (e.g., 10 microns, 20 microns, 50 microns, 100 microns) and about 20 or more microns long (e.g., 30 microns, 40 microns, 50 microns, 75 microns, 100 microns, 200 microns, 500 microns). Furthermore, the separation between adjacent electrode elements can vary. In some embodiments, the separation between adjacent electrodes is greater than the electrode's width. The separation can be, for example, more than about 10 microns (e.g., 20 microns, 30 microns, 50 microns, 100 microns, 200 microns, or more).

Although interdigitated electrodes 800 includes 10 electrode elements, other embodiments can have fewer or more electrode elements (e.g., more than 20 elements, 50 elements, 100 elements).

While polynomial and interdigitated electrode geometries have been described, in general, any electrode geometry that provides a desired electric field profile can be used.

In some embodiments, electrode array 230 includes multiple electrode regions, each electrode region being configured to apply an electrode field to a different sample of particles. In particular, electrode array 230 can be configured for use with an array of samples, such as for use with a 96-well plate. In the case of a 96-well plate, electrode array 230 includes an 8×12 array of electrode regions, each region corresponding to a sample in the 96-well plate. Such embodiments can provide high sample throughput as the system can be configured to automatically study each of the samples in sequence, with minimal additional user input after initial configuration. In general, electrode array 230 can include any number of electrode regions (e.g., less than 96, or more than 96, such as 384).

DEP system 100 can also include devices with which to apply additional forces to the particles. For example, DEP system 100 can include devices for applying hydrodynamic force, centrifugal force, gravitational force, ultrasonic force, electrophoretic force, magnetic force, and/or an optical force to one or more of the particles in the dispersion. For example, to apply an optical force, an output beam from a laser can be focused through the microscope objective lens to provide an optical trap in the chamber. A hydrodynamic force can be applied by flowing a liquid through the chamber at a predetermined rate. An example of a device for applying an ultrasonic force is an ultrasonic transducer, which can be coupled to the chamber. To apply a centrifugal force, one could rotate the chamber at a rotational velocity sufficient to apply the desired force.

Alternatively, or additionally, DEP system 100 can include additional probes to monitor various parameters in the chamber that can affect the dielectrophoretic response. For example, DEP system can include a conductivity sensor to monitor the conductivity of the sample in the chamber during dielectrophoretic study. In some embodiments, DEP system 100 can include a thermometer to monitor the temperature of the sample. Other parameters that might affect the dielectrophoretic response that can be monitored include dielectric permittivity, pH value, fluid viscosity, and/or the material or chemical treatment of the electrode and/or chamber walls.

Personal computer 130 can monitor additional parameters of the system that can affect the dielectrophoretic response of the particles. For example, by including a temperature probe on electrode array and connecting the probe to it, the PC can be used to monitor the temperature of the dispersion during DEP manipulation. PC 130 can monitor other parameters, such as those mentioned above.

In the described embodiment, images are detected using CCD camera 120, however, other types of detectors can also be used (e.g., CMOS imaging chips or optical waveguides). Furthermore, in some implementations, the PC computer and image capture card can be replaced by a custom electronic processor designed to analyze signals from the detector using signal processing techniques.

In the described embodiment, optical microscope 110 is an upright transmission mode configured for bright field imaging. However, other modes of optical microscopy can also be used, including, for example, dark field microscopy, fluorescence microscopy, and/or confocal microscopy. More generally, the above-described techniques can be applied in conjunction with and/or using non-microscopic modes of data capture, for example, CCD arrays, CMOS arrays, or using a plate reader.

A number of embodiments of the invention have been described. Nevertheless, it will be understood that various modifications may be made without departing from the spirit and scope of the invention. Accordingly, other embodiments are within the scope of the following claims.

What is claimed is:

1. A method, comprising:
sequentially applying an AC electric field at a plurality of frequencies to a medium in a chamber, the medium comprising one or more particles suspended in a fluid;
tracking the location of the one or more particles in the chamber while applying the AC electric field;

calculating a velocity of each of the one or more tracked particles at each electric field frequency from the locations, wherein calculating the velocity of a particle comprises normalizing the velocity based on the location of the particle; and determining a characteristic of the one or more particles from the calculated velocities.

2. The method of claim 1, wherein the characteristic of the one or more particles determined from the calculated velocities is related to the dielectric polarization of the one or more particles.

3. The method of claim 2, further comprising measuring a size of each of the one or more particles.

4. The method of claim 3, wherein measuring the size of each of the one or more particles comprises acquiring an image of the one or more particles in the chamber and determining the sizes from the image.

5. The method of claim 4, wherein determining the sizes from the image comprises determining a figure of merit for a particle in the image.

6. The method of claim 5, wherein determining the sizes from the image comprises optimizing the figure of merit.

7. The method of claim 1, wherein tracking the location of the one or more particles comprises acquiring a series of images of the one or more particles at each frequency.

8. The method of claim 7, wherein tracking the location of each of the one or more particles further comprises identifying the one or more particles in the series of images at a frequency.

9. The method of claim 1, wherein determining the characteristic of the one or more particles comprises determining the dielectrophoretic cross-over frequency for the particles.

10. The method of claim 9, wherein determining the dielectrophoretic cross-over frequency for the one or more particles comprises using a parametric fitting function that relates particle velocity to frequency.

11. The method of claim 10, wherein the parametric fitting function comprises at least three fitting parameters.

12. The method of claim 1, wherein determining the characteristic of the one or more particles comprises determining a frequency or range of frequencies where the one or more particles experience a maximum positive dielectrophoretic force.

13. The method of claim 12, wherein calculating a velocity of each of the one or more particles comprises calculating multiple velocity values of the velocity at the frequency or in the range of frequencies where the one or more particles experience a maximum positive dielectrophoretic force.

14. The method of claim 1, wherein determining the characteristic of the one or more particles comprises determining a frequency or range of frequencies where the one or more particles experience a maximum negative dielectrophoretic force.

15. The method of claim 14, wherein calculating a velocity of each of the one or more particles comprises calculating multiple velocity values of the velocity at the frequency or in the range of frequencies where the one or more particles experience a maximum negative dielectrophoretic force.

16. The method of claim 1, wherein the applied electric field is generated by a waveform comprising a sinusoidal waveform.

17. The method of claim 1, wherein the applied electric field is generated by a digitally synthesized waveform.

18. The method of claim 1, wherein the one or more particles comprise particles that are labeled with a fluorescent moiety.

19. The method of claim 1, further comprising treating the medium with a chemical or physical agent and determining an effect of the treatment on the characteristic of the one or more particles as a function time.

20. The method of claim 1, further comprising treating a surface adjacent the medium with an agent to modify the interaction of one or more of the particles with the surface.

21. The method of claim 20, wherein the agent causes the surface to selectively adhere or repel one or more of the particles.

22. The method of claim 20, further comprising determining an effect of the treatment on the characteristic of the one or more particles as a function of time.

23. The method of claim 1, further comprising identifying any of the one or more particles that form a pearl chain.

24. The method of claim 23, wherein the characteristic is determined from particles that do not form a pearl chain.

25. A method, comprising:
sequentially applying an AC electric field at a plurality of frequencies to a medium in a chamber, the medium comprising one or more particles suspended in a fluid;
tracking the location of the one or more particles in the chamber while applying the AC electric field;
calculating a velocity of each of the one or more tracked particles at each electric field frequency from the locations, wherein calculating the velocity of a particle comprises normalizing the velocity based on the size of the particle; and
determining a characteristic of the one or more particles from the calculated velocities.

26. A method, comprising:
sequentially applying an AC electric field at a plurality of frequencies to a medium in a chamber, the medium comprising one or more particles suspended in a fluid;
tracking the location of the one or more particles in the chamber while applying the AC electric field;
calculating a velocity of each of the one or more tracked particles at each electric field frequency from the locations, wherein calculating the velocity of a particle comprises normalizing the velocity based on the electric field strength at the particle's location; and
determining a characteristic of the one or more particles from the calculated velocities.

27. The method of claim 26, wherein the electric field strength is determined using a computer model.

28. The method of claim 27, wherein the computer model accounts for a finite thickness of the electrode elements.

29. A method, comprising:
sequentially applying an AC electric field at a plurality of frequencies to a medium in a chamber, the medium comprising one or more particles suspended in a fluid;
tracking the location of the one or more particles in the chamber while applying the AC electric field;
calculating a velocity of each of the one or more tracked particles at each electric field frequency from the locations, wherein calculating the velocity of a particle comprises normalizing the velocity based on the electric field gradient at the particle's location; and
determining a characteristic of the one or more particles from the calculated velocities.

30. The method of claim 29, wherein the electric field gradient is determined using a computer model.

31. A method, comprising:
sequentially applying an AC electric field at a plurality of frequencies to a medium in a chamber, the medium comprising a plurality of particles suspended in a fluid;

measuring a velocity of each of the plurality of particles at each electric field frequency, wherein measuring the velocity of a particle comprises normalizing the velocity of the particle based on a characteristic of the particle or a characteristic of the electric field at the particle's location; and determining a dielectrophoretic cross-over frequency for the particles from the measured velocities.

32. The method of claim 33, wherein the velocity of the particle is normalized based on the electric field gradient at the particle's location.

33. A method, comprising:
sequentially applying an AC electric field at a plurality of frequencies to a medium in a chamber, the medium comprising a plurality of particles suspended in a fluid;
acquiring a series of images of the plurality of particles at each frequency;
measuring a velocity of each of the plurality of particles at each electric field frequency, wherein measuring the velocity of a particle comprises normalizing the velocity of the particle based on a characteristic of the particle or a characteristic of the electric field at the particle's location; and
measuring a size of each of the plurality of particles.

34. The method of claim 33, further comprising determining a cross-over frequency for the particles from the measured velocities.

35. The method of claim 34, wherein determining a cross-over frequency for the plurality of particles comprises determining an individual cross-over frequency for each of the plurality of particles and statistically analyzing the individual cross-over frequencies.

36. The method of claim 33, wherein measuring the velocity of each of the plurality of particles comprises monitoring positions of the plurality of particles in each of the series of images.

37. The method of claim 36, wherein measuring the velocity of each particle comprises determining the change in position of each particle in between images.

38. The method of claim 33, wherein the velocity of the particle is normalized based on the location of the particle.

39. The method of claim 33, wherein the velocity of the particle is normalized based on the size of the particle.

40. The method of claim 33, wherein the velocity of the particle is normalized based on the electric field strength at the particle's location.

41. A method, comprising:
sequentially applying an AC electric field at a plurality of frequencies to a medium in a chamber, the medium comprising a plurality of particles suspended in a fluid;
electronically acquiring a series of images of the plurality of particles at each frequency; and
determining a cross-over frequency for the particles from the images, wherein the cross-over frequency is determined based on normalized velocities calculated for each of the plurality of particles.

42. A method, comprising:
sequentially applying an AC electric field at a plurality of frequencies to a medium in a chamber, the medium comprising a plurality of particles suspended in a fluid;
acquiring a series of images of the plurality of particles at each frequency; and
determining a velocity for each particle from each series of images, wherein determining the velocity of a particle comprises normalizing the velocity of the particle based on a characteristic of the particle or a characteristic of the electric field at the particle's location.

43. A system for performing dielectrophoretic analysis on a population of particles, the system comprising:
a chamber having a wall;
a plurality of electrodes disposed on the wall of the chamber;
a function generator configured to supply an AC voltage to the plurality of electrodes;
a detector configured to acquire images of a sample disposed in the chamber; and
an electronic controller in electrical communication with the detector,
wherein during operation of the system the function generator sequentially supplies an AC voltage to the plurality of electrodes at a plurality of frequencies while the detector acquires a series of images of a sample in the chamber, the sample comprising one or more particles suspended in a fluid, and the electronic controller tracks the location of the one or more particles in the chamber, calculates a velocity of each of the one or more particles at each electric field frequency from the tracked locations, and determines a first characteristic of the one or more particles from the calculated velocities,
and wherein calculating a velocity of a particle comprises normalizing the velocity of the particle based on a second characteristic of the particle or a characteristic of the electric field at the particle's location.

44. The system of claim 43, further comprising an optical microscope positioned relative to the chamber to image the sample to an image plane.

45. The system of claim 44, wherein the detector is positioned at the image plane.

46. The system of claim 43, wherein the electrodes comprise polynomial electrodes.

47. The system of claim 43, wherein the electrodes comprise interdigitated electrodes.

48. The system of claim 43, wherein the plurality of electrodes comprise an array of electrode regions.

49. The system of claim 48, wherein the array of electrode regions comprises an 8×12 array of electrode regions.

50. The system of claim 43, wherein the velocity of the particle is normalized based on the location of the particle.

51. The system of claim 43, wherein the velocity of the particle is normalized based on the size of the particle.

52. The system of claim 43, wherein the velocity of the particle is normalized based on the electric field strength at the particle's location.

53. The system of claim 43, wherein the velocity of the particle is normalized based on the electric field gradient at the particle's location.

* * * * *